(12) United States Patent
Linares et al.

(10) Patent No.: US 8,926,705 B2
(45) Date of Patent: Jan. 6, 2015

(54) IMPLANTABLE JOINT ASSEMBLY FEATURING DEBRIS ENTRAPMENT CHAMBER SUBASSEMBLIES ALONG WITH OPPOSING MAGNETIC FIELDS GENERATED BETWEEN ARTICULATING IMPLANT COMPONENTS IN ORDER TO MINIMIZE FRICTIONAL FORCE AND ASSOCIATED WEAR

(71) Applicants: Miguel A. Linares, Bloomfield Hills, MI (US); Linares Medical Devices, LLC, Auburn Hills, MI (US)

(72) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 177 days.

(21) Appl. No.: 13/632,512

(22) Filed: Oct. 1, 2012

(65) Prior Publication Data

US 2013/0030537 A1 Jan. 31, 2013

Related U.S. Application Data

(63) Continuation-in-part of application No. 12/776,903, filed on May 10, 2010, now Pat. No. 8,828,088.

(60) Provisional application No. 61/542,406, filed on Oct. 3, 2011.

(51) Int. Cl.
  *A61F 2/30* (2006.01)
  *A61F 2/38* (2006.01)
  *A61F 2/08* (2006.01)
  *A61F 2/32* (2006.01)

(52) U.S. Cl.
  CPC .......... *A61F 2/30771* (2013.01); *A61F 2/3804* (2013.01); *A61F 2/08* (2013.01);
  (Continued)

(58) Field of Classification Search
  CPC .............. A61F 2/34; A61F 2002/2821; A61F 2002/30079
  USPC ............ 623/18.11, 21.13, 21.16, 2.17, 21.18, 623/16.11, 18.12, 20.2, 20.23, 201.11, 623/21.15, 23.39
  See application file for complete search history.

(56) References Cited

U.S. PATENT DOCUMENTS 2,667,644 A    2/1954   Johnson
3,140,712 A *   7/1964   Hunter ........................ 623/18.12

(Continued)

OTHER PUBLICATIONS

International Search Report—International application No. PCT/US2011/042624.

*Primary Examiner* — Thomas J Sweet
*Assistant Examiner* — Seema Mathew
(74) *Attorney, Agent, or Firm* — Gifford, Krass, Sprinkle, Anderson & Citkowski, P.C.

(57) ABSTRACT

A multi-component joint assembly incorporated into reconditioned end surfaces established between a first bone and opposing second bone. A first component is anchored into a reconditioned end surface of the first bone and exhibits a first exposed support surface. A second component is anchored into a reconditioned end surface of at least one of radius and ulna bones and exhibits a second exposed support surface. An intermediate component is supported in articulating fashion between the first and second anchored components. A plurality of micro debris entrapment chamber subassemblies are incorporated into the components and communicate with at least one of the articulating surfaces for isolating and capturing debris resulting from joint wear.

11 Claims, 4 Drawing Sheets

(52) U.S. Cl.
CPC ............... *A61F 2/03965* (2013.01); *A61F 2/32* (2013.01); *A61F 2/38* (2013.01); *A61F 2002/30673* (2013.01); *A61F 2002/30682* (2013.01); *A61F 2002/30807* (2013.01); *A61F 2002/30823* (2013.01); *A61F 2002/30827* (2013.01); *A61F 2002/30934* (2013.01); *A61F 2002/30937* (2013.01); *A61F 2002/30971* (2013.01); *A61F 2002/30079* (2013.01)
USPC ............... 623/18.12; 623/16.11; 623/18.11; 623/20.11; 623/20.14; 623/20.2; 623/20.22; 623/20.23; 623/21.11; 623/21.15

(56) References Cited

U.S. PATENT DOCUMENTS

| | | | |
|---|---|---|---|
| 3,651,521 A | 3/1972 | Devas | |
| 3,798,679 A | 3/1974 | Ewald | |
| 3,875,594 A | 4/1975 | Swanson | |
| 3,964,106 A | 6/1976 | Hutter, Jr. et al. | |
| 4,214,322 A * | 7/1980 | Kraus | 623/23.49 |
| 4,215,439 A | 8/1980 | Gold et al. | |
| 4,231,122 A | 11/1980 | Koeneman | |
| 4,328,593 A | 5/1982 | Sutter et al. | |
| 4,367,562 A | 1/1983 | Gauthier et al. | |
| 4,538,305 A | 9/1985 | Engelbrecht et al. | |
| 4,714,477 A | 12/1987 | Fichera et al. | |
| 4,950,298 A | 8/1990 | Gustilo et al. | |
| 4,964,868 A | 10/1990 | Bloebaum | |
| 4,990,161 A | 2/1991 | Kampner | |
| 5,007,934 A | 4/1991 | Stone | |
| 5,021,061 A | 6/1991 | Wevers et al. | |
| 5,092,898 A | 3/1992 | Bekki et al. | |
| 5,171,325 A | 12/1992 | Aulie | |
| 5,197,987 A | 3/1993 | Koch et al. | |
| 5,389,107 A | 2/1995 | Nassar et al. | |
| 5,462,362 A | 10/1995 | Yuhta et al. | |
| 5,509,934 A | 4/1996 | Cohen | |
| 5,553,476 A | 9/1996 | Oehy et al. | |
| 5,571,193 A | 11/1996 | Kampner | |
| 5,593,445 A * | 1/1997 | Waits | 623/23.42 |
| 5,645,601 A | 7/1997 | Pope et al. | |
| 5,662,158 A | 9/1997 | Caldarise | |
| 5,676,702 A | 10/1997 | Ratron | |
| 5,702,476 A | 12/1997 | Limacher et al. | |
| 5,728,175 A | 3/1998 | Rincoe | |
| 5,800,566 A | 9/1998 | Gramnas | |
| 5,879,386 A * | 3/1999 | Jore | 623/16.11 |
| 5,879,406 A | 3/1999 | Lilley | |
| 5,879,407 A | 3/1999 | Waggener | |
| 5,916,269 A | 6/1999 | Serbousek et al. | |
| 5,921,358 A | 7/1999 | Gramnas | |
| 6,045,581 A | 4/2000 | Burkinshaw | |
| 6,165,223 A | 12/2000 | Metzger et al. | |
| 6,364,910 B1 * | 4/2002 | Shultz et al. | 623/19.13 |
| 6,398,815 B1 | 6/2002 | Pope et al. | |
| 6,627,141 B2 | 9/2003 | McNulty et al. | |
| 6,660,040 B2 | 12/2003 | Chan et al. | |
| 6,692,679 B1 | 2/2004 | McNulty et al. | |
| 6,723,102 B2 | 4/2004 | Johnson et al. | |
| 6,800,298 B1 | 10/2004 | Burdick et al. | |
| 6,800,670 B2 | 10/2004 | Shen et al. | |
| 6,811,568 B2 | 11/2004 | Minamikawa | |
| 6,818,172 B2 | 11/2004 | King et al. | |
| 6,849,076 B2 | 2/2005 | Blunn et al. | |
| 6,866,685 B2 | 3/2005 | Chan et al. | |
| 6,962,607 B2 | 11/2005 | Gundlapalli et al. | |
| 7,044,983 B1 | 5/2006 | Cheng | |
| 7,066,958 B2 | 6/2006 | Ferree | |
| 7,087,091 B1 | 8/2006 | Chen | |
| 7,109,181 B2 | 9/2006 | Cowlen et al. | |
| 7,148,209 B2 | 12/2006 | Hoemann et al. | |
| 7,175,666 B2 | 2/2007 | Yao | |
| 7,179,298 B2 | 2/2007 | Greenlee | |
| 7,186,364 B2 | 3/2007 | King et al. | |
| 7,294,150 B1 | 11/2007 | Mandell et al. | |
| 7,331,995 B2 | 2/2008 | Eisermann et al. | |
| 7,384,430 B2 | 6/2008 | Greer et al. | |
| 7,578,851 B2 | 8/2009 | Dong et al. | |
| 7,771,485 B2 | 8/2010 | Grundei | |
| 7,780,738 B2 | 8/2010 | Khandkar et al. | |
| 8,062,376 B2 * | 11/2011 | Shultz et al. | 623/19.13 |
| 8,176,922 B2 | 5/2012 | Sherman et al. | |
| 8,273,130 B2 * | 9/2012 | Gradl | 623/18.12 |
| 8,398,718 B2 | 3/2013 | Richardson et al. | |
| 8,454,692 B2 * | 6/2013 | Fleischmann | 623/16.11 |
| 8,702,801 B2 * | 4/2014 | Linares | 623/20.15 |
| 8,702,802 B2 * | 4/2014 | Linares et al. | 623/20.21 |
| 8,801,796 B2 * | 8/2014 | Rogachefsky | 623/21.14 |
| 2002/0128651 A1 * | 9/2002 | Hyde, Jr. | 606/60 |
| 2002/0183845 A1 | 12/2002 | Mansmann | |
| 2003/0065401 A1 | 4/2003 | Amrich et al. | |
| 2003/0114935 A1 | 6/2003 | Chan et al. | |
| 2003/0130740 A1 | 7/2003 | Stocks et al. | |
| 2003/0216669 A1 | 11/2003 | Lang et al. | |
| 2004/0024460 A1 | 2/2004 | Ferree | |
| 2004/0068322 A1 | 4/2004 | Ferree | |
| 2005/0055100 A1 | 3/2005 | Lewis et al. | |
| 2005/0171604 A1 | 8/2005 | Michalow | |
| 2005/0192672 A1 | 9/2005 | Wyss et al. | |
| 2005/0192674 A1 | 9/2005 | Ferree | |
| 2005/0287187 A1 | 12/2005 | Mansmann | |
| 2006/0015186 A1 | 1/2006 | Isaac | |
| 2007/0156246 A1 * | 7/2007 | Meswania et al. | 623/19.12 |
| 2007/0179613 A1 | 8/2007 | Heinz | |
| 2007/0225818 A1 * | 9/2007 | Reubelt et al. | 623/19.12 |
| 2007/0287027 A1 | 12/2007 | Justin et al. | |
| 2008/0033567 A1 | 2/2008 | Stchur | |
| 2008/0288081 A1 | 11/2008 | Scrafton et al. | |
| 2009/0076605 A1 | 3/2009 | Linares | |
| 2009/0125108 A1 | 5/2009 | Linares | |
| 2009/0216333 A1 * | 8/2009 | Wolfe et al. | 623/21.12 |
| 2010/0331993 A1 * | 12/2010 | Gradl | 623/23.4 |
| 2013/0079886 A1 * | 3/2013 | Linares et al. | 623/21.16 |
| 2014/0188230 A1 * | 7/2014 | Rogachefsky | 623/18.12 |

* cited by examiner

IMPLANTABLE JOINT ASSEMBLY FEATURING DEBRIS ENTRAPMENT CHAMBER SUBASSEMBLIES ALONG WITH OPPOSING MAGNETIC FIELDS GENERATED BETWEEN ARTICULATING IMPLANT COMPONENTS IN ORDER TO MINIMIZE FRICTIONAL FORCE AND ASSOCIATED WEAR

CROSS REFERENCE TO RELATED APPLICATIONS

The present application claims the priority of U.S. Ser. No. 61/542,406 filed Oct. 3, 2011, and is further a continuation in part of U.S. Ser. No. 12/776,903, filed May 10, 2010.

FIELD OF THE INVENTION

The present invention discloses an artificial joint assembly capable of being implanted into reconditioned bone ends defining any suitable joint, including without limitation such as elbow, hip, knee shoulder or ankle joints. The implant combines multiple artificial components incorporated into first and second reconditioned bone end surfaces for providing increased wear life in tandem with evenly distributed wear pattern/profile as well as enhanced flexibility and mobility.

Additional features include debris entrapment pockets defined at spaced locations along any one or more of the wear surfaces associated with the implantable components and which are designed for collecting and isolating micro sized debris particles resulting from implant and bone wear.

Additional variants include the generation of either fixed or adjustable electromagnetic forces between the various implant components. In one variant, static magnetic fields are generated in the spherical portion and surrounding bone end face mounted implants. In a further, a central electromagnet defines a core of the spherical portion and is constructed such that it continuously recharges in response to rotational movement associated with the joint and, in response generates a continuous electromagnetic force in relation to alternately charged layers (North-South) associated with both the surface proximate layers of the spherical insert and opposing concave seating surfaces of the bone end installed components. The configuration of the electromagnetic fields (and associated Lorentz forces) are such that opposing forces are established at the articulating zones defined between the spherical inter-supporting implant component and the opposing concave surfaces of the upper and lower bone defining end mounted implants, as well as secondarily associated with an inner inter rotating layer defined within the spherical component, this resulting in reduced joint wear and friction at the articulating interfaces.

BACKGROUND OF THE RELEVANT ART

The prior art is documented with examples of medical prosthetic implant assemblies such as defining replacement joints. One example is depicted in the wear resistant ball and socket joint of Waggener, U.S. Pat. No. 5,879,407, which includes biologically inert ball and socket components exhibiting different hardness levels and which is configured to minimize wear and chemical, electrochemical and mechanical deterioration in the environment of the human body.

Other examples include the system and method depicted in Sherman, U.S. Pat. No. 8,176,922, for a bi-directional communication within an implantable medical device using an implant component as an antenna and which interfaces with an external data communication device. In a monopole antenna configuration, a ground plane is established so that the electromagnetic field emitted by the implant component is reflected and the emitted and reflected fields resemble the emitted field of a dipole antenna for the carrier frequency.

Blunn et al., U.S. Pat. No. 6,849,076, teaches a surgical distraction device for applying an extending or tensioning force non-invasively to a patient's skeleton or to an implant which includes anchoring means for attaching first and second components of the device to a bone or to adjoining bones. The components are connected by a linkage of an extendable length, a magnet connected to the linkage via a reduction gearbox and actuating means located externally of the patient for generating a moving or varying electro-magnetic field, thereby causing the magnet to rotate and the linkage to be extended.

SUMMARY OF THE PRESENT INVENTION

The present invention discloses a multi-component joint assembly incorporated into reconditioned end surfaces established between a first bone and at least one opposing second bone. A first component is anchored into a reconditioned end surface of the first bone and exhibits a first exposed support surface.

A second component is anchored into a reconditioned end surface of at least one of the radius and ulna bones and exhibits a second exposed support surface. An intermediate component is supported in at least one of eccentric or rotational articulating fashion between the first and second anchored components. In one non-limiting variant, a plurality of micro debris entrapment chamber subassemblies are incorporated into at least one of the components and communicate with at least one of the articulating surfaces for isolating and capturing debris resulting from joint wear.

Additional features include each of the entrapment chamber subassemblies having a constricted perimeter location separating a joint zone entryway with an enlarged interior. A pair of rubberized membranes are secured to perimeter edge locations of each of the entryway locations, these being caused to be inwardly deflected in response to in-flow pressure forces resulting from normal joint articulation, further resulting in pass through of the debris into the enlarged interiors where they are segregated away from the wear zone of the joint.

Additional features include the membranes incorporating a magnetically charged zone for exerting an attraction force on a metallic or polymeric/metallic shaving or particle. The intermediate component may also include a spherical shaped component and each of the anchored components may further exhibit a concave surface for supporting the intermediate component. Each of the first, second and intermediate components may also be constructed of at least one of a metal, plastic, polymer or composite material.

In a further variant, an electromagnetic force is established between the intermediate component and at least one of the first and second anchored components and includes opposite polarities established between at least a surface layer of the intermediate component and the anchored components in order to create a cushioning and impact force reducing layer along articulating surfaces between the components. The intermediate component may exhibit a spherical shaped element incorporating a core magnet exhibiting a first polarity which defines a static electromagnetic generating force along with an outer surface layer exhibiting an opposite polarity.

Outer layers associated with each of the anchored components exhibit an opposing force generating polarity relative to a polarity associated with the intermediate component. The intermediate component can again exhibit a spherical shaped element including a continuously recharging core electromagnet, an insulating layer surrounding the core electromagnet, with at least one polarity charged external layer. In an additional variant, an algorithm is integrated into the core electromagnet and, in response to varying joint load impact forces determined at the articulating interface established between the intermediate component and anchored components, generates an adjustable opposing force in order to maintain a desired separation profile between the components.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As will be disclosed with succeeding reference to FIGS. 1-5, the present invention discloses a representative artificial joint assembly incorporated into an elbow according to one non-limiting application. As previously indicated, the micro debris entrapment subassemblies and opposing generated electromagnetic forces are capable of being integrated into any suitable and in situ reconditioned joint assembly not limited to the elbow illustrated, but additionally including any of the knee, shoulder, hip, ankle, wrist, etc. According to any disclosed variant, the implant assembly combines multiple artificial components incorporated into first and second reconditioned joint defining surfaces for providing increased wear life in tandem with evenly distributed wear pattern/ profile as well as enhanced flexibility and mobility.

The above said, and referring again to the drawings, the joint assembly described herein is particularly configured for such as in situ reconditioned installation within a patient's elbow (between the lower end of the upper humerus bone and corresponding upper ends of the lower radius and ulna bones), however it is further understood that certain applications could in theory include other joint applications, either human or other mammalian. For purposes of ease and clarify of illustration, the various embodiments depicted further do not include reference to additional necessary components of the elbow joint, such as including associated muscles, tendons and ligaments, the inclusion of which are assumed and which collectively define a functioning and articulating elbow.

Figure 1:
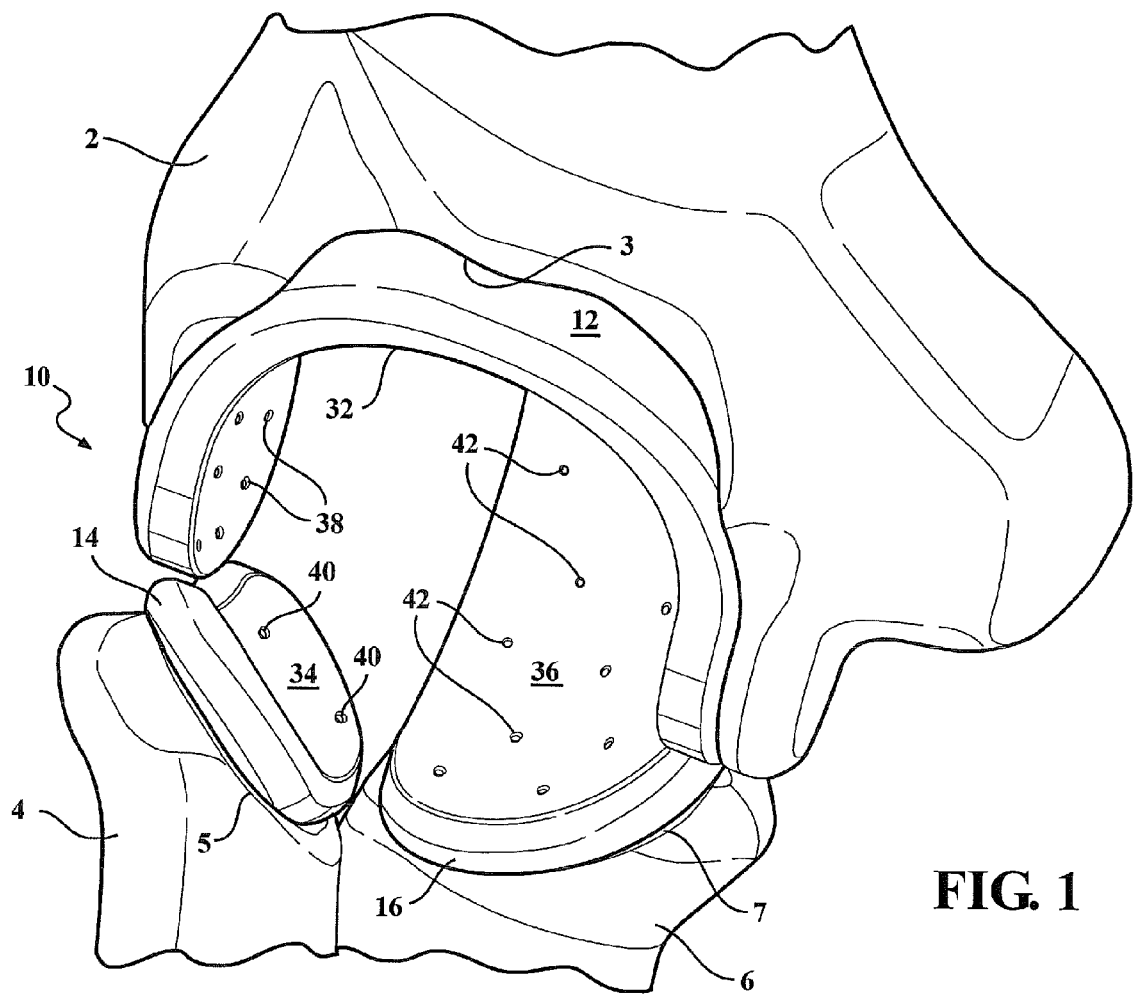
FIG. 1 is a perspective view of a representative elbow implant assembly according to a first embodiment of the invention, with spherical inter-supported component removed, and better illustrating the reconditioned upper and lower bone end face mounted implant components with micro debris entrapment chamber subassemblies.
Figure 2:
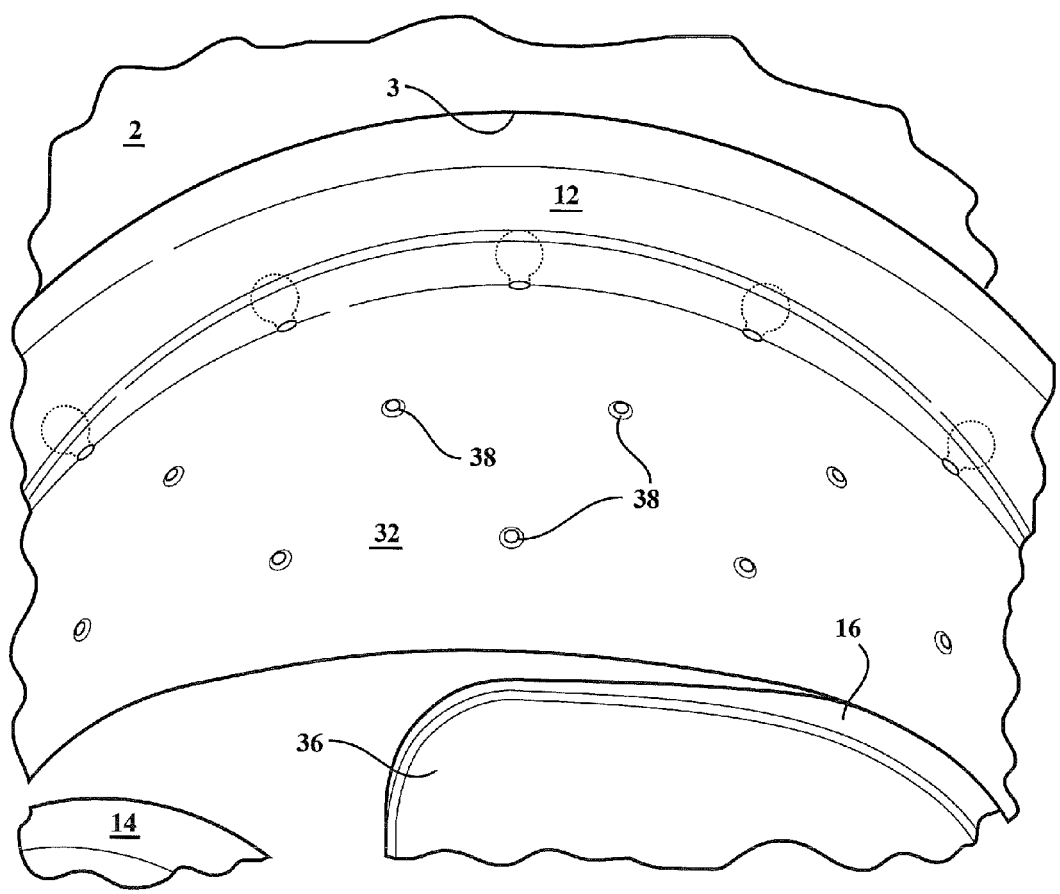
FIG. 2 is an enlarged and rotated perspective view of the assembly in FIG. 1 and better depicting the arrangement of debris entrapment subassemblies incorporated into the upper humerus end face mounted implant component.

Referring now to FIG. 1, a perspective view is generally shown at 10 of an elbow implant assembly according to a first embodiment of the invention and which is incorporated between an upper arm (humerus) bone 2 and a lower arm bones represented by radius 4 and ulna 6. Although not shown in exploded fashion, each of the bone ends is reconditioned, such as in situ during a surgical procedure involving the installation of the joint assembly, and by the use of appropriate drilling, shaping, boring and surfacing tools as is known in the surgical industry and by which a series of appropriately concave shaped end facing profiles are established at 3, 5 and 7 respectively for each of the humerus 2, radius 4 and ulna 6 end faces.

Such reconditioning occurs following incision or removal of any remaining damaged bone and/or cartilage associated with the damaged joint and during an appropriate surgical procedure again utilizing medical drilling, boring and shaping instruments in order to recondition the joint defining bone ends and to create the desired shaping and profile of the joint. As previously indicated, it is advantageous to refashion the joint end profiles in situ during an appropriate surgical procedure, a further objective being to retain or repair, where possible, natural ligament, cartilage and muscle associated with a normal functioning joint.

Although not shown, such reconditioning can be employed with minimal interference to such necessary additional elements of the elbow joint 9 (as depicted in the non-limiting example of FIGS. 1-5) and including associated ligaments, muscles and tendons. Without limitation, it is further understood that the joint assemblies described in each of the illustrated variants can be integrated into either of human or synthetic bones (such as which can also contemplate both human and synthetic bones in a single joint application), with such joint assemblies also capable of surgically implanted in either total or partial fashion concurrent with any necessary degree of refashioning or removal of damaged bone or joint. This can further include reconditioning of both the radius 4 and ulna 6 (as again depicted by resurfaced end profiles 5 and 7) with the further understanding that only the ulna need be refaced in certain applications.

Referring again collectively to FIGS. 1, 2, 4 and 5 the multi-component assembly 10 better illustrates the reconditioned end-configurations 3, 5 and 7 (again best shown in FIGS. 4-5) established between the upper humerus 2 and lower radius 4 and ulna 6 bones. A set of bone end installable implant portios are depicted at 12, 14 and 16 with each exhibiting (as best shown in cutaway views of FIGS. 4 and 5) a rear facing profile suitable for anchoring into the respective reconditioned end face configuration 3, 5 and 7.

Each of the implant portions 12, 14 and 16 are constructed of any arrangement of metal, polymer, plastic, composite or other suitable material, with it further being understood that the individual pairs of components can be arrayed with any pattern of alternating materials, such that the components 12, 14 and 16 can be constructed of a first material, with an intermediate and inter-positioned spherical shaped bearing or ball portion 18 (see again in cutaway in FIGS. 4 and 5) positioned therebetween being constructed of a second material. In this fashion, the desired wear properties and profiles are adjusted in part based upon the material selection of the individual components with concurrent objectives being both equalization of overall wear patterns established between the respective pairs of components and determining those situations in which metal on metal or plastic on plastic contact between the components is either desired or, more often, not.

A suitable medical adhesive, cement or other fastener can be employed for securing each of the upper component 12 and lower components 14 and 16 into the respective reconditioned joint defining ends 3, 5 and 7 of the humerus 2, radius 4 and ulna 6. As further best shown in cutaway FIGS. 4-5, each of the reconditioned bone ends includes an interior extending aperture, including aperture 20 associated with reconditioned humerus 2 end face 3, as well as smaller and corresponding apertures 22 and 24 associated with the reconditioned radius 4 end face 5 and ulna 6 end face 7. In this manner, a rearward extending anchoring stem (see at 26 for upper implant component 12 and further at 28 and 30 for lower implant components 14 and 16) is configured for seating within the associated bone end face interior aperture, thereby assisting in seating the end mounted implants in the manner depicted in FIGS. 1 and 2.

Each of the end face mounted implants 12, 14 and 16 exhibits a concave exterior facing profile defined by exposed concave support faces 32, for upper implant 12, and at 34 and 36 for lower implants 14 and 16 (again FIG. 1) such that, upon securing the implants 12, 14 and 16 within the reconditioned end face locations 3, 5 and 7 of the bones 2, 4 and 6, these collectively define upper and lower seating locations for supporting the interposed spherical element 18 in a designed range of eccentric articulating fashion.

As further previously noted, the concave spherical supporting faces 28, 30 and 32 can each be constructed of a smooth lubricant entrained or other polished plastic, composite or metal surface, with the exterior configuration of the spherical support 18 again being constructed of an alternating material, such as to reduce and equalize wear profiles, as well as to enhance operational range and effectiveness.

As again previously indicated, additional configurations of muscles, ligaments, tendons are provided and can include both natural and/or synthetic materials which can be implanted or reconstructed in order to provide a dynamic and long-term implantable assembly. Also, the seating or inserting rear faces of the end face mounted implant portions 12, 14 and 16 as best shown in FIG. 3 further include an undercut textured or otherwise roughened consistency, this contributing to promotion of bone marrow in-growth into the implant portions following such as initial adhesive and seating affixation, such bone growth contributing to long term retention of the implant.

Referring again to FIG. 1, with subsequent reference again to FIGS. 2 and 3, each of the implants 12, 14 and 16, individual pluralities of micro debris entrapment chamber subassemblies, see reference to narrowed entryway locations at 38, 40 and 42, and which are arranged in spaced apart fashion across the surfaces 32, 34 and 36 of the upper 12 and lower 14 and 16 implants. As better shown with reference to succeeding FIGS. 2 and 3, the entrapment chambers each exhibit volumetric defining interiors (shown in non-limited fashion as generally cylindrical in two dimensional cutaway in FIGS. 2 and 3) in the instance of the upper humerus end face mounted implant 12. Although not shown, it is further understood that additional entrapment chambers may be likewise incorporated into the interposed spherical element (not shown).

Figure 3:
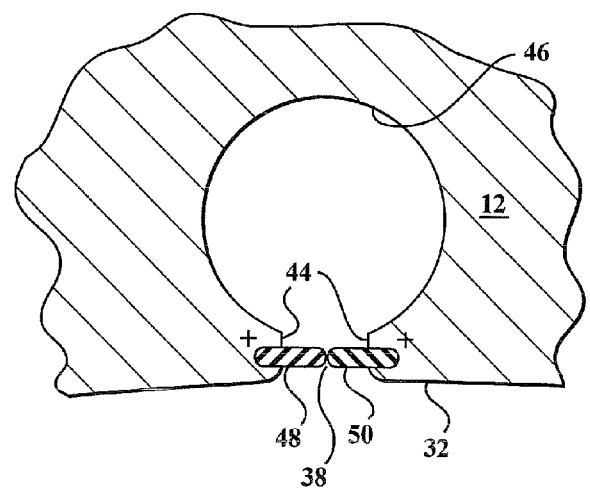
FIG. 3 is a schematic two dimensional cutaway of a selected debris entrapment subassembly illustrating rubberized membranes located at narrowed entryway locations and which, in response to in-flow pressure forces resulting from normal joint articulation, results in inward deflection of the membranes by micro sized wear shavings or debris (both bone and implant) and resultant entrapment and isolation within the inner defined pockets.

FIG. 3 is a schematic two dimensional cutaway of a selected debris entrapment subassembly associated with the upper humerus mounted implant 12 and illustrating a narrowed or constricted perimeter location 44 separating the joint zone entryway 38 with the enlarged interior which is further defined by spherical interior surface 46. A pair of rubberized membranes 48 and 50 are provided at the narrowed entryway location 44 (such as secured to perimeter edge locations of the narrowed entryway location 44) and, in non-deflected positions, define a mating boundary therebetween which isolates the enlarged interior. In one operational configuration, the inner opposing extending membranes are caused to be inwardly deflected, relative to their anchored locations as best shown in FIG. 3 and in response to in-flow pressure forces resulting from normal joint articulation, this resulting in pass through of micro sized wear shavings or debris (such as associated with both the bone and implants) into the enlarged interior 46.

Upon the membranes 48 and 50 deflecting back to their closed position, the micro sized debris (such as in any dimensional range capable of passing though the narrowed entryways down to 0.005") are entrapped and isolated within the inner defined pockets so that they do not otherwise further degrade or impair the operation of the joint zone. It is further envisioned that the membrane locations can include a magnetically charged zone, as referenced at ++ at narrowed perimeter location 44 in FIG. 3, and which can exert an attraction force on a metallic or polymeric/metallic shaving or particle which may have become detached over time and is free floating within the joint zone. The ability to remove micro sized debris and particles resulting from extended use of the joint further results in longer life for the implant, along with reductions in patient discomfort and undesirable noises (including squeaking) which can otherwise result from buildup of debris within the joint zone.

Figure 4:
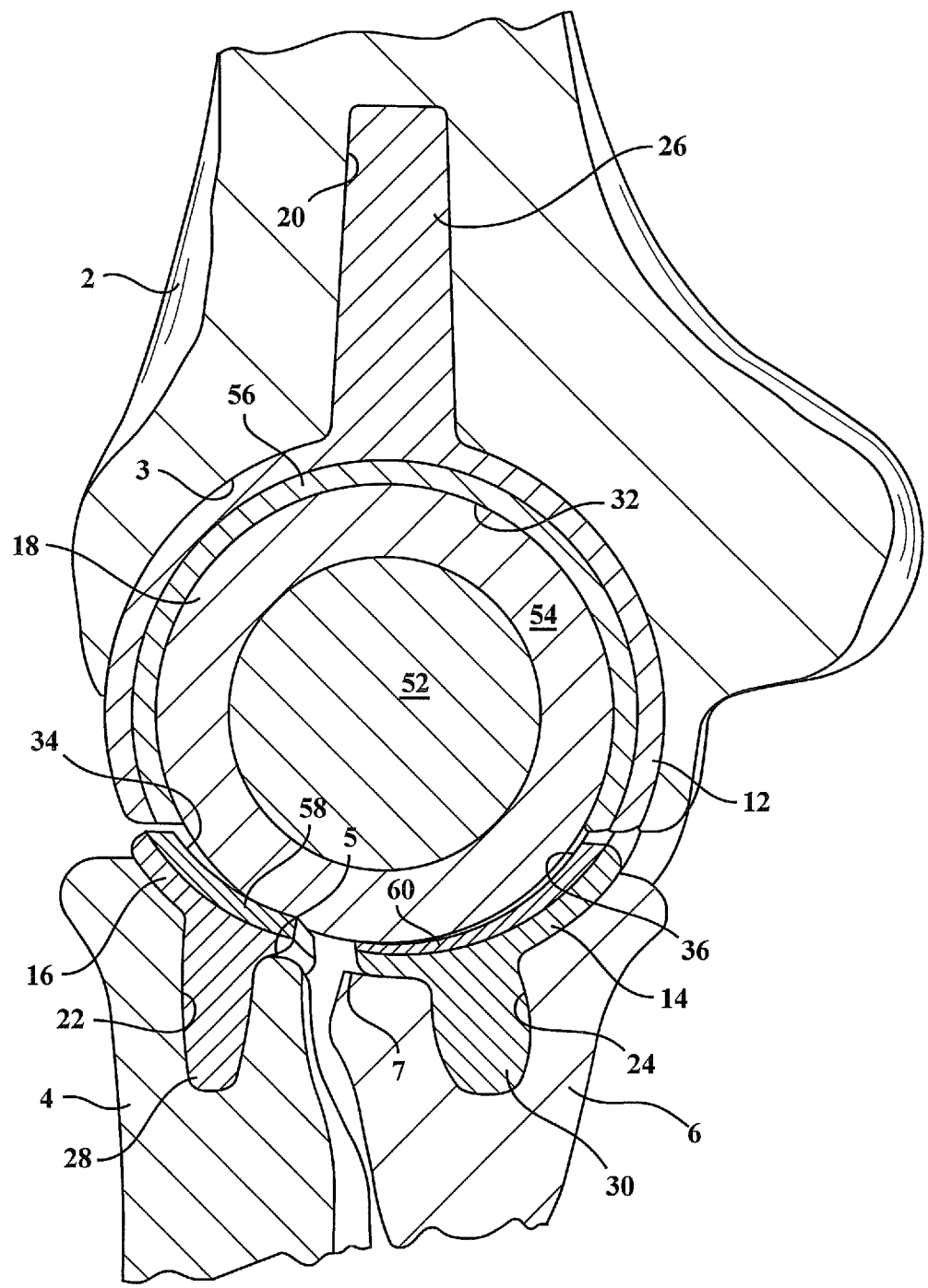
FIG. 4 is a sectional view of an assembled elbow joint and depicting a first variant of electromagnetic force components in which static (i.e. continuous or non-changing) electromagnetic forces are established between the spherical inter-disposed portion and the end face mounted bone implant portions.

Referring now to FIG. 4, the sectional cutaway view of the assembled elbow joint depicts a first variant of electromagnetic force components in which a constant or static (i.e. continuous or non-changing) electromagnetic force, also termed Lorentz force, is established between the spherical inter-disposed portion 18 and the end face mounted bone implant portions 14 and 16. The spherical element 18 includes a core magnet 52, such as exhibiting a first polarity (represented as North), and which defines a static electromagnetic generating force along with an outer layer 54 exhibiting an opposite polarity (represented as South).

As further shown by the cutaway depictions of the various implants 12, 14 and 16, each can likewise include multiple (e.g. at least two) layers in which an outer layer (such as a softened plastic composite entrained with a magnetically chargeable component) is provide as depicted at 56 for upper implant 12 and further at 58 and 60 for each of lower implants 14 and 16. The surface layers 56, 58 and 60 each exhibit a selected polarity charge, such as South for all three layers 56, 58 and 60. An opposing North magnetic polarity is established relative to the core magnet 52 and, optionally, the surface layer 54 of the spherical component 18, this resulting in a continuous and separating cushion for both limiting inter component contact such as at the interface between the core 52 and/or surface layer 54 and the 56-58-60 surface layers of the components 12-14-16 (including friction reduction), thus resulting in increased wear.

Figure 5:
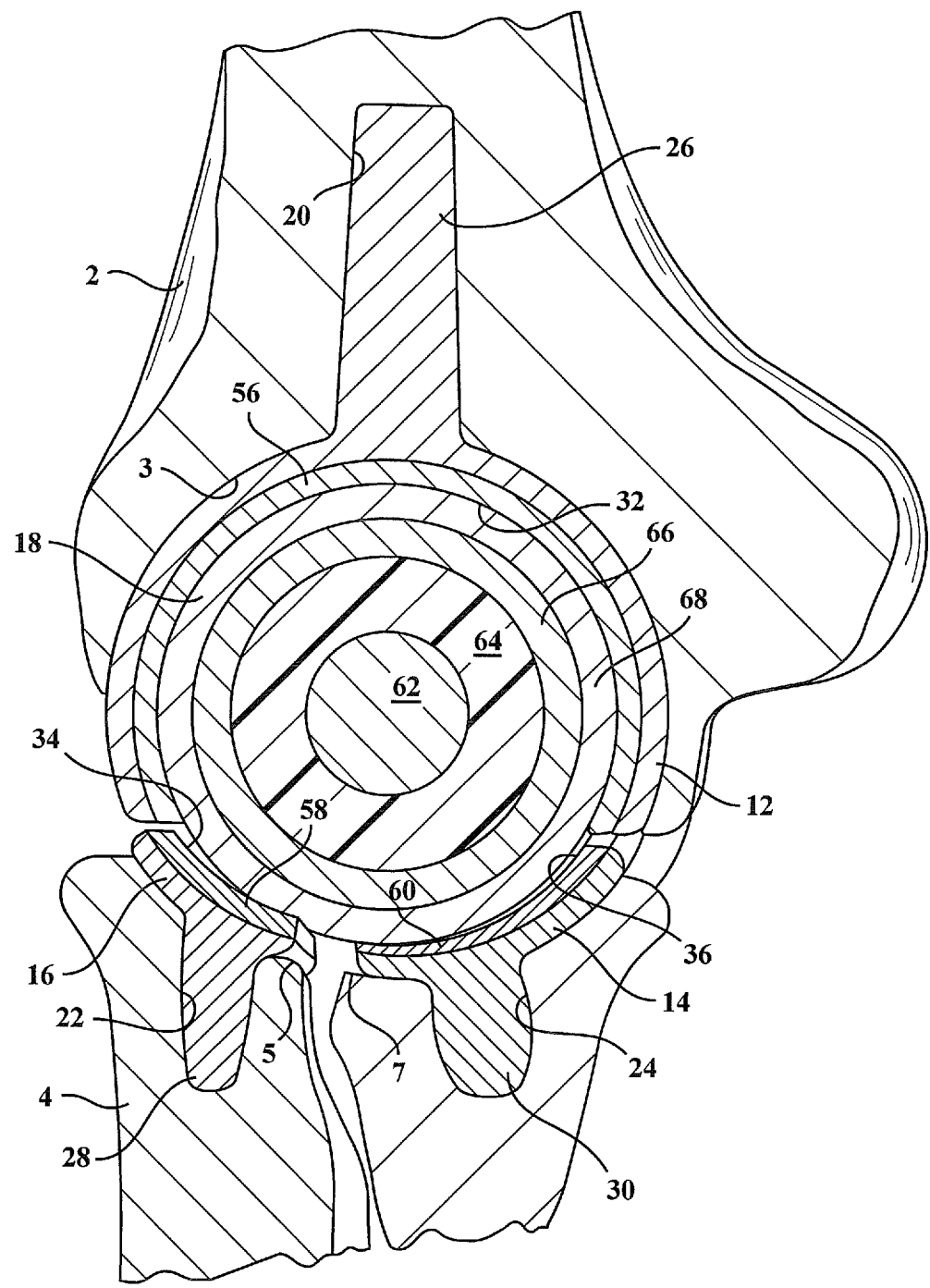
FIG. 5 is a like sectional view of a second variant of electromagnetic force components in which a central electromagnet defines a core of the spherical portion and is constructed such that it continuously recharges in response to rotational movement associated with the joint and, in response generates a continuous electromagnetic force in relation to alternately charged layers (North-South) associated with both the surface proximate layers of the spherical insert and opposing concave seating surfaces of the bone end installed components.

Finally, and referring to FIG. 5, a like sectional view is shown of a second variant of electromagnetic force components in which a central electromagnet 62 defines a core of the spherical portion 18 and is constructed with components not unlike those contained within a motion rechargeable watch and such that it likewise continuously recharges a stored battery (not shown) in response to rotational movement associated with the joint. Surrounding the electromagnet 62 is an insulating layer 64, over which are arranged successive North 66 and South 68 charged layers. The implants again include outermost South charged surface layers 56, 58 and 60 which, in opposition to the South polarity of the spherical member outer layer 68, generates an opposing electromagnetic magnetic force so as to create a separation layer or cushion at the joint interfaces between the spherical element and each of the upper 12 and lower 14 and 16 implants.

The design of the electromagnet 62 is further such that it includes an algorithm integrated into its construction which, in response to varying joint load impact forces determined at the eccentric interface established between outer spherical layer 68 and opposing implant surface layers 56, 58 and 60, generates an adjustable or vary-able electromagnetic force by varying a draw from the built in battery and thereby modulating the strength of the magnetic fields and resultant opposing Lorentz forces, these in response to determined changes in the compressive forces determined at the eccentric joint zone and in order to maintain a desired separation profile.

Having described my invention, other and additional preferred embodiments will become apparent to those skilled in the art to which it pertains, and without deviating from the scope of the appended claims.

We claim:

1. A multi-component joint assembly incorporated into reconditioned end surfaces established between a first bone and at least one opposing second bone, said assembly comprising:
   a first component adapted to being anchored into the reconditioned end surface of the first bone and exhibiting a first exposed support surface;
   a second component is adapted to being anchored into a reconditioned end surface of at least one of the second bones and exhibiting a second exposed support surface;
   an intermediate component supported in at least one of eccentric or rotational articulating fashion between said first and second anchored components; and
   a plurality of micro debris entrapment chamber subassemblies incorporated into at least one of said components and communicating with at least one of said articulating surfaces for isolating and capturing debris resulting from joint wear, each of said entrapment chamber subassemblies further including a constricted perimeter location separating a joint zone entryway with an enlarged interior, a pair of rubberized membranes secured to perimeter edge locations of said entryway location being caused to be inwardly deflected in response to in-flow pressure forces resulting from normal joint articulation, resulting in pass through of said debris into said enlarged interiors.

2. The joint assembly as described in claim 1, further comprising said membranes incorporating a magnetically charged zone for exerting an attraction force on a metallic or polymeric/metallic shaving or particle.

3. The joint assembly as described in claim 1, said intermediate component further comprising a spherical shaped component.

4. The joint assembly as described in claim 1, each of said anchored components further exhibiting a concave surface for supporting said intermediate component.

5. The joint assembly as described in claim 1, each of said first, second and intermediate components further being constructed of at least one of a metal, plastic, polymer or composite material.

6. A multi-component joint assembly incorporated into reconditioned end surfaces established between a first bone and at least one opposing second bone, said assembly comprising:
   a first component adapted to being anchored into the reconditioned end surface of the first bone and exhibiting a first exposed support surface;
   a second component adapted to being anchored into a reconditioned end surface of at least one of the second bones and exhibiting a second exposed support surface;
   an intermediate component supported in at least one of eccentric or rotational articulating fashion between said first and second anchored components;
   an electromagnetic force established between said intermediate component and at least one of said first and second anchored components includes opposite polarities established between at least a surface layer of said intermediate component and said anchored components in order to create a cushioning and impact force reducing layer along articulating surfaces between said components; and
   said intermediate component further including a spherical shaped element including a continuously recharging core electromagnet, an insulating layer surrounding said core electromagnet, with at least one polarity charged external layer, an algorithm integrated into said core electromagnet and, in response to varying joint load impact forces determined at said articulating interface established between said intermediate component and anchored components, generating an adjustable opposing force in order to maintain a desired separation profile between said components.

7. The joint assembly as described in claim 6, said intermediate component further comprising a spherical shaped element incorporating a core magnet exhibiting a first polarity which defines a static electromagnetic generating force along with an outer surface layer exhibiting an opposite polarity.

8. The joint assembly as described in claim 6, further comprising outer layers associated with each of said anchored components exhibiting an opposing force generating polarity relative to a polarity associated with said intermediate component.

9. An artificial elbow implant assembly incorporated into reconditioned opposing end surfaces of each of an upper humerus bone and lower radius and ulna bones, said implant assembly comprising:
   a first implant component adapted to being anchored into the reconditioned end surface of the humerus bone and exhibiting a first concave shaped and magnetically chargeable surface layer;
   second and third components adapted to being anchored into the reconditioned end surfaces of each of the radius and ulna bones in opposing fashion to said first implant component, said second and third components exhibiting second and third concave shaped and magnetically chargeable surface layers; and a spherical shaped intermediate component incorporating a core magnet and supported in an articulating fashion between said magnetically chargeable surface layers such that, in response to alternating a polarity charge applied to said magnetically chargeable surface layers and said core magnet, a continuous and separating cushion force is created between said components resulting in reduction in inter-abrading friction and increased wear life a plurality of micro debris entrapment chamber subassemblies incorporated into at least one of said components and communicating with at least one of said articulating surfaces for isolating and capturing debris resulting from joint wear, wherein each of said entrapment chamber subassemblies further comprises a constricted perimeter location separating a joint zone entryway with an enlarged interior, a pair of rubberized membranes secured to perimeter edge locations of said entryway location being caused to be inwardly deflected in response to in-flow pressure forces resulting from normal joint articulation, resulting in pass through of said debris into said enlarged interiors.

10. The implant assembly as described in claim 9, further comprising said membranes incorporating a magnetically charged zone for exerting an attraction force on a metallic or polymeric/metallic shaving or particle.

11. The implant assembly as described in claim 9, said spherical shaped intermediate component further comprising a pair of outer most magnetically charged layers surrounding said core magnet and in opposing electromagnetic force communicating fashion with said magnetically chargeable surface layers of said first, second and third implant components.

* * * * *